United States Patent [19]

Burdeska

[11] 4,208,513
[45] Jun. 17, 1980

[54] BENZOXAZOLYL-PHENYLSTILBENES, PROCESSES FOR PRODUCING THEM, AND THEIR USE AS OPTICAL BRIGHTENERS

[75] Inventor: Kurt Burdeska, Basel, Switzerland

[73] Assignee: Ciba-Geigy Corporation, Ardsley, N.Y.

[21] Appl. No.: 955,687

[22] Filed: Oct. 30, 1978

[30] Foreign Application Priority Data

Nov. 10, 1977 [LU] Luxembourg .................. 78483

[51] Int. Cl.² ........................................... C07D 263/54
[52] U.S. Cl. ........................... 542/459; 252/301.24
[58] Field of Search ........................ 542/459, 460; 252/301.24

[56] References Cited

U.S. PATENT DOCUMENTS

| 3,732,221 | 5/1973 | Siegrist et al. | 542/459 |
| 3,781,278 | 12/1973 | Siegrist et al. | 542/459 |
| 3,850,914 | 11/1974 | Luthi | 542/459 |
| 3,926,963 | 12/1975 | Meyer | 542/459 |
| 3,993,645 | 11/1976 | Crounse et al. | 542/459 |
| 3,996,210 | 12/1976 | Fleck et al. | 542/459 |
| 4,014,870 | 3/1977 | Meyer | 542/454 |
| 4,032,558 | 6/1977 | Fleck et al. | 542/459 |

FOREIGN PATENT DOCUMENTS

| 1299470 | 7/1974 | Switzerland | 542/459 |
| 1363607 | 8/1974 | United Kingdom | 542/459 |
| 1388102 | 3/1975 | United Kingdom | 542/459 |

Primary Examiner—Arthur P. Demers
Attorney, Agent, or Firm—Prabodh I. Almaula

[57] ABSTRACT

Benzoxazolyl-phenyl stilbenes of the formula

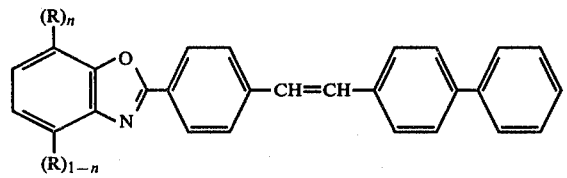

wherein
n is the number 0 or 1, and
R is halogen, phenyl, phenoxy or alkyl having 2 to 4 C atoms and, if n is the number 1, also methoxy.

9 Claims, No Drawings

BENZOXAZOLYL-PHENYLSTILBENES, PROCESSES FOR PRODUCING THEM, AND THEIR USE AS OPTICAL BRIGHTENERS

The present invention relates to novel benzoxazolyl-phenyl stilbenes, to processes for producing them, and also to their use for optically brightening natural and synthetic organic materials.

Benzoxazolyl-phenyl stilbenes are already known from the U.S. Pat. No. 3,850,914 and 3,781,278, and from the Swiss Auslegeschrift No. 9052/69.

The novel benzoxazolyl-phenyl stilbenes correspond to the formula

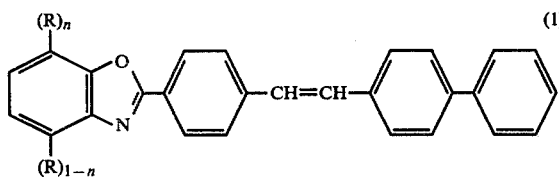
(1)

wherein
n is the number 0 or 1, and
R is halogen, phenyl, phenoxy or alkyl having 2 to 4 C atoms and, if n is the number 1, also methoxy.

To be emphasised within the scope of the compounds of the formula I are those of the formula

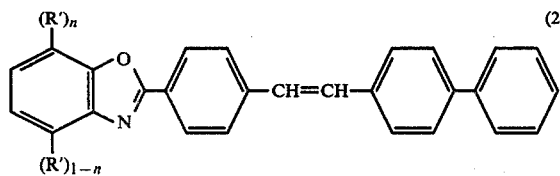
(2)

wherein
n is the number 0 or 1, and
R' is chlorine, phenyl, phenoxy, sec-butyl or tert-butyl.

Of particular importance are the compounds of the formulae

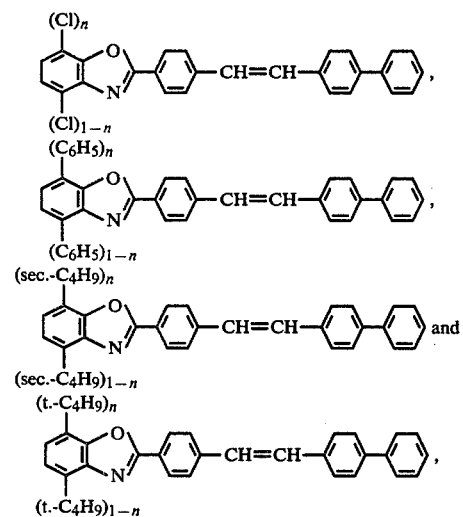

in which formulae the symbol n is 0 or 1.

The benzoxazolyl-phenyl stilbenes according to the invention can be produced in a manner known per se, for example by reaction of a compound of the formula

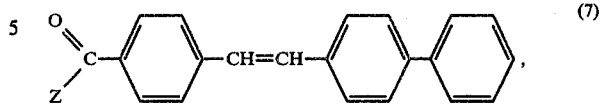
(7)

wherein Z is hydroxyl or halogen, with an aminophenol of the formula

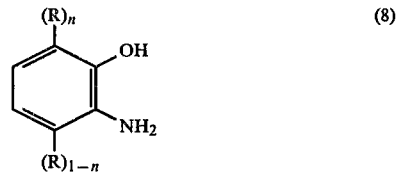
(8)

wherein R and n have the meanings defined in the foregoing.

The reaction between the respective components of the formulae (7) and (8) can be performed, with or without intermediate separation of the acid amide intermediates firstly occurring, by heating to elevated temperatures, for example to 120° to 350° C., advantageously in an inert gas, for example in a stream of nitrogen, and the reaction is optionally carried out in the presence of a catalyst. Suitable catalysts are for example: boric acid, boric anhydride, zinc chloride and p-toluenesulfonic acid, and also polyphosphoric acids including pyrophosphoric acid. If boric acid is used as the catalyst, it is used advantageously in an amount of 0.5 to 5%, relative to the total weight of the reaction mixture. It is also possible to concomitantly use high-boiling organic solvents, such as dimethylformamide, dichlorobenzene, trichlorobenzene and aliphatic, optionally etherified, oxy compounds, for example propylene glycol, ethylene glycol monoethyl ether or diethylene glycol diethyl ether, and high-boiling esters of phthalic acid, for example dibutyl phthalate.

If the process is performed in two stages, it is possible to firstly condense carboxylic acid halides of the formula (7) with the o-amino compound of the formula (8) in the presence of an inert organic solvent, such as toluene, xylenes, chlorobenzene, dichlorobenzene, trichlorobenzene or nitrobenzene, at temperatures between 100° and 200° C.; and to then convert the resulting acyl compounds at temperatures between 150° and 350° C., optionally in the presence of a catalyst, into the final product according to the formula (1). If carboxylic acid chlorides are used as starting materials, they can be produced directly before condensation with the o-amino compound, from the free carboxylic acid and thionyl chloride (optionally with the addition of a catalyst, such as pyridine) in the solvent, in which the condensation reaction subsequently occurs.

A further important method of production consists in synthesis according to the "Anil synthesis" principle. In this case, a Schiff base of the formula

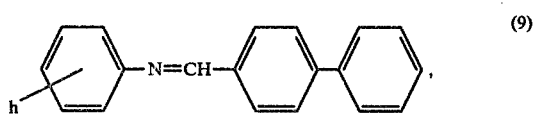
(9)

wherein h is advantageously hydrogen or chlorine, is reacted with a methyl compound of the formula

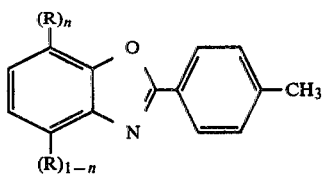

wherein R and n are as defined in the foregoing, in the presence of a strongly basic alkali compound in dimethylformamide as the reaction medium. By strongly basic alkali compounds are meant in this case those compounds of the alkali metals which have a basicity value of at least approximately that of lithium hydroxide. They can accordingly be compounds of lithium, sodium, potassium rubidium or cesium, for example of the alcoholate, hydroxide or strongly basic ion-exchanger type. There are advantageously used potassium compounds of the composition

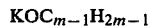

wherein m is an integer from 1 to 6 inclusive, such as potassium hydroxide or potassium tertiary butylate. In the case of alkali alcoholates, the reaction is to be performed in a virtually anhydrous medium, whereas in the case of alkali hydroxides, water contents of up to 25% (for example crystal water contents) are permitted. With regard to potassium hydroxide, a water content of up to about 10% has proved advantageous. The following may be mentioned as examples of other applicable alkali compounds: sodium methylate, sodium hydroxide, lithium hydroxide, rubidium hydroxide, cesium hydroxide, and so forth. It is obviously also possible to work with mixtures of bases of this kind.

The compounds of the formula (10) are advantageously reacted with the Schiff base in equivalent amounts, so that there is no appreciable excess of either component. It is of advantage to use at least the equivalent amount of the alkali compound, that is, at least 1 mol of a compound having for example a KO group to 1 mol of a Schiff base. With the use of potassium hydroxide, the 4- to 8-fold amount is preferably employed. The reaction can generally be performed at temperatures in the range between about 10° and 150° C. Where alcoholates are used as potassium compound in the reaction, no addition of heat is in general necessary. The procedure is for example such that the Schiff base is added to the mixture of the compound of the formula (10), the solvent and the potassium alcoholate, advantageously with stirring and with the exclusion of air, at a temperature of between 15° and 30° C., whereupon the reaction straight away occurs with a slight increase of temperature. When potassium hydroxide is used, it is frequently necessary to perform the reaction at higher temperature. For example, the reaction mixture is slowly heated to 30° to 100° C., and then held for some time, for example ½ to 2 hours, at this temperature. The final materials can be isolated from the reaction mixture by customary methods known per se.

Benzoxazolyl-phenyl stilbenes of the formula (1) can be produced also by reacting a compound of the formula

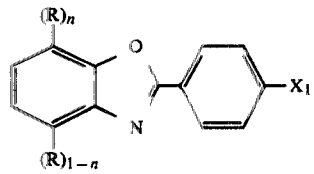

with a compound of the formula

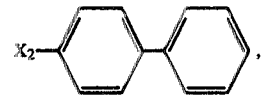

wherein R and n are as defined in the foregoing, and one of the symbols $X_1$ and $X_2$ is a —CHO group, and the other is a grouping of the formula

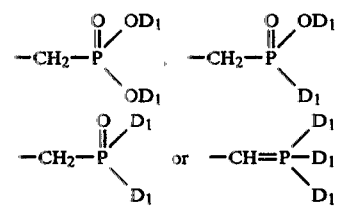

wherein $D_1$ is an unsubstituted or substituted alkyl, aryl, cycloalkyl or aralkyl group, in dimethylformamide and in the presence of a strong base.

This production process is advantageously performed in inert solvents. Examples of these which may be given are: hydrocarbons such as toluene and xylene, or alcoholates such as methanol, ethanol, isopropanol, butanol, glycols, glycol ethers such as 2-methoxyethanol, hexanols, cyclohexanol and cyclooctanol, also ethers such as diisopropyl ether, tetrahydrofuran and dioxane, as well as dimethylsulfoxide, formamide and N-methylpyrrolidone. Polar organic solvents, such as dimethyl formamide and dimethylsulfoxide, are particularly suitable. Some of the reactions may be performed also in an aqueous solution.

The temperature at which the reaction can be performed can vary within wide limits. It is determined:

(α) by the stability of the employed solvent to the the reactants, especially to the strongly basic alkali compounds;

(β) by the reactivity of the condensation constituents, and (γ) by the effectiveness of the solvent-base combination as a condensation agent.

Temperatures which can be used in practice are in general between about 10° and 100° C., particularly when dimethylformamide or dimethylsulfoxide is employed as the solvent. The preferred temperature range is between 20° and 60° C.

Suitable strongly basic alkali compounds are in particular the hydroxides, amides and alcoholates, (preferably such primary alcohols containing 1 to 4 carbon atoms) of the alkali metals, with those of lithium, sodium and potassium being of primary interest for reasons of economy. Also alkali sulfides and alkali carbonates, aryl alkali compounds such as phenyl lithium, or strongly basic amines (including ammonium bases), for example trialkylammonium hydroxides, can however be successfully used in particular cases.

The novel compounds defined in the foregoing exhibit in the dissolved or finely dispersed state a more or less pronounced fluorescence. They can be used for optically brightening the widest variety of synthetic, semi-synthetic or natural organic materials, or substances containing organic materials of this kind.

The following groups of organic materials, so far as an optical brightening thereof is concerned, may for example be given, but the summary is not intended to express any limitation with regard to the organic materials which can be optically brightened by the novel compounds of the present invention:

I. Synthetic organic high-molecular materials (a) polymerisation products based on organic compounds containing at least one polymerisable carbon-carbon double bond, i.e., homo- or copolymers thereof and also products thereof which have received an aftertreatment, for example cross-linkage, graft or degradation products, polymer blends, or products obtained by modification of reactive groups, for example polymers based on $\alpha,\beta$-unsaturated carboxylic acids or derivatives of such carboxylic acids, especially on acrylic compounds (such as acrylic esters, acrylic acid, acrylonitrile, acrylic amides, and derivatives or methacrylic analogues thereof), or olefin hydrocarbons (such as ethylene, propylene, styrenes or dienes, also so-called ABS polymers), polymers based on vinyl and vinylidene compounds (such as vinyl chloride, vinyl alcohol or vinylidene chloride);

(b) polymerisation products obtainable by ring opening, for example polyamides of the polycaprolactam type, also polymers which can be obtained both by way of polyaddition and by way of polycondensation, such as polyethers or polyacetals;

(c) polycondensation products or precondensates based on bi- or polyfunctional compounds having groups that can be condensed, their homo- and co-condensation products, and also products of an aftertreatment, for example polyesters, particularly saturated polyesters (for example ethylene glycol terephthalic acid polyesters) or unsaturated polyesters (for example maleic acid/dialcohol polycondensates and also their cross-linkage products with polymerisable vinyl monomers), unbranched and also branched polyesters (also polyesters based on alcohols of higher valence, such as alkyd resins), polyesters, polyamides (for example hexamethylenediamine-adipate), maleic resins, melamine resins, precondensates and analogues thereof, polycarbonates and silicones; and (d) polyaddition products such as polyurethanes (cross-linked and not cross-linked) and epoxide resins.

The organic materials to be optically brightened can be in the most varied stages of processing (raw materials, semimanufactured articles or finished articles). They can alternatively be in the form of the widest variety of shaped articles, for example in the form of mainly three-dimensionally extended objects, such as plates, profiles or injection-moulded articles, various work pieces, chips, granules or foam plastics, also in the form of predominantly two-dimensionally shaped objects, such as films, sheets, lacquers, coatings or impregnations, or in the form mainly of unidimensionally shaped objects, such as filaments, fibres, flocks or threads. The said materials can on the other hand be in the unshaped condition in the most varied homogeneous or inhomogeneous forms of dispersion, for example in the form of powders, solutions, emulsions, dispersions, latex, pastes or waxes.

Fibre materials can be in the form for example of endless filaments (stretched or unstretched), staple fibres, flocks, hanks, textile filaments, yarns, twines, fibre fleeces, felts, cotton-wool or flock articles, or in the form of textile fabrics or textile composite materials, knitted fabrics and also paper, cardboard or paper pulp.

The compounds to be used according to the invention are important inter alia for the treatment of textile organic materials, especially textile fabrics. If fibres, which can be in the form of staple fibres or continuous filaments, hanks, fabrics, knitted goods, fleeces, flock carriers or composite materials, are to be optically brightenes according to the invention, this is performed advantageously in an aqueous medium, in which the respective compounds are present in a finely dispersed form (suspensions, so-called microdispersions or optionally solutions). Dispersing agents, stabilisers, wetting agents and further auxiliaries can be added if necessary during the treatment.

Depending on the brightener-compound type used, it may prove advantageous to perform the process in a neutral or alkaline or acid bath. The treatment is usually performed at temperatures of about 20° to 140° C., for example at the boiling temperature of the bath or near to the boiling temperature (about 90° C.). For the processing, according to the invention, of textile substrates, solutions or emulsions in organic solvents are also suitable, as is practiced in the dyeing industry in the case of so-called solvent dyeing (padding/thermofixing application or exhaust dyeing in dyeing machines. The benzoxazolyl-phenyl stilbenes according to the invention are particularly suitable for the above-mentioned padding/thermofixing application.

The novel optical brighteners according to the present invention can also be added to, or incorporated into, the materials before or during shaping thereof. Thus, for example, in the production of films, sheets (for example rolling into polyvinyl chloride, polyamide or polystyrene in the hot state) or moulded articles, the novel optical brighteners can be added to the moulding materials or to the injection-moulding compounds.

When the shaping of fully- or semi-synthetic organic materials is carried out by spinning processes or by way of spinning solutions, the optical brighteners can be applied by the following processes:

addition to the starting substances (for example monomers) or to the intermediate products (for example precondensates, prepolymers), that is to say, before or during polymerisation, polycondensation or polyaddition;

powdering onto polymer chips or granules for spinning solutions;

bath dyeing of polymer chips or granules for spinning solutions;

controlled (dosed) addition to spinning melts or spinning solutions; and application to tow before stretching or drawing.

Among the novel brighteners according to the present invention, the 7-phenyl-benzoxazolyl-phenyl-stilbene and also the 4-phenyl-benzoxazolyl-phenyl-stilbene are excellently suitable for the optical brightening of polyester fibres before the shaping thereof.

Furthermore, the brighteners according to the present invention, and particularly the polyamide materials brightened therewith, have exceptionally good fastness to light.

The novel optical brighteners according to the present invention can be used for example in the following forms:

(a) mixtures with dyes (shading) or with pigments (coloured or in particular for example white pigments) or as additives to dye baths, printing pastes, etching pastes or resist pastes; also for the aftertreatment of dyeings, printings or etchings;

(b) in admixture with so-called "carriers", wetting agents, plasticisers, swelling agents, antioxidants, light stabilisers, heat stabilisers and chemical bleaching agents (chlorite bleaching or bleaching-bath additives);

(c) in admixture with cross-linking agents, finishing agents (for example starch or synthetic finishing agents) and also in combination with the widest range of textile finishing processes, especially synthetic resin finishings (for example noncreasing finishes, such as 'wash-and-wear', 'permanent-press' and 'no-iron'), also flameproof, soft-handle and anti-soiling, or antistatic finishes or antimicrobial finishes;

(d) incorporation of the optical brighteners into polymer carrier materials (polymerisation, polycondensation or polyaddition products) in the dissolved or dispersed form for application for example in coating, impregnating or binding agents (solutions, dispersions and emulsions) for textiles, fleeces, paper or leather);

(e) additives to so-called master batches;

(f) additives to the widest variety of industrial products in order to render these more marketable (for example improvement in the appearance of soaps, detergents and pigments);

(g) in combination with other substances having an optically brightening action;

(h) in spinning-bath preparations, that is, as additives to spinning baths, as are used for improving the sliding properties in the case of the further processing of synthetic fibres, or from a special bath for the stretching of fibres;

(i) as scintillators for various purposes of a photographic nature, such as for electrophotographic reproduction or for supersensitisation; and (j) depending on substitution, as laser dyes.

If the brightening process is combined with textile-treatment methods or finishing methods, the combined treatment can in many cases be advantageously carried out with the aid of suitable stable preparations which contain the optically brightening compounds at a concentration high enough to ensure that the desired brightening effect is obtained.

In certain cases, the full action of the brighteners is brought out by an aftertreatment. This can be for example a chemical treatment (e.g. an acid treatment), a thermal treatment (e.g. heat) or a combined chemical/thermal treatment. For example, in the optical brightening of a range of fibre substrates, for example of polyester fibres, with the brighteners according to the invention, the procedure advantageously adopted comprises impregnating these fibres with the aqueous dispersions (optionally also solutions) of the brighteners at temperatures below 75° C., for example at room temperature; and then subjecting the impregnated fibres to a dry heat treatment at temperatures above 100° C.; it is in general recommended that the fibre material be dried beforehand at moderately elevated temperature, for example at at least 60° C. to about 130° C. The heat treatment in the dry state is then advantageously performed at temperatures between 120° and 225° C., for example by heating in a drying chamber, by ironing in the given temperature range, or by treatment with dry superheated steam. The drying and the dry heat treatment can also be carried out directly one after the other, or they can be combined in a single operation.

The amount of novel optical brighteners to be used, relative to the material to be optically brightened, can vary within wide limits. Even with very small amounts, in certain cases for example of 0.0001 percent by weight, an evident and durable effect is obtained. It is however also possible to use amounts of up to about 0.8 percent by weight, and if need be up to about 2 percent by weight. For most practical requirements, however, amounts preferably of between 0.0005 and 0.5 percent by weight are used.

The benzoxazolyl-phenyl stilbenes according to the invention are particularly suitable for optically brightening polyesters and polyester/cotton mixtures by the exhaust process.

It is frequently advantageous for various reasons not to use the brighteners as such, that is to say, not in the pure form, but in admixture with the most varied auxiliaries and diluting agents, for example anhydrous sodium sulfate, sodium sulfate decahydrate, sodium chloride, sodium carbonate, alkali metal phosphates, such as sodium orthophosphate and potassium orthophosphate, sodium pyrophosphate and potassium pyrophosphate and sodium tripolyphosphates or potassium tripolyphosphates, or alkali metal silicates.

In the Examples which follow, percentages are always given as percent by weight, and, except where otherwise stated, melting and boiling points are uncorrected.

EXAMPLE 1

13.3 g of 2-(4'-diethylphosphonomethylphenyl)-7-chlorobenzoxazole, 7.65 g of diphenyl-4-aldehyde and 100 ml of dimethylformamide are heated at 40° C. To the solution which has formed is added at 40° to 45° C., within 25 minutes, 2.5 g of sodium methylate, and the reaction mixture is stirred at this temperature for a further 3 hours. It is subsequently cooled to room temperature, neutralised with formic acid, and then stirred into 1000 ml of water. The product which has precipitated is filtered off, washed with water and with methanol, and dried in vacuo to yield 13.5 g of the compound of the formula

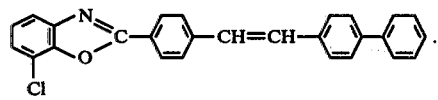 (100)

The product crystallises from xylene, with the addition of bleaching earth, in the form of slightly greenish-yellow crystals having a melting point of 212° to 213° C.

The 2-(4'-diethylphosphonomethylphenyl)-7-chlorobenzoxazole required as starting product is produced in the following manner:

158.5 g of 2-(4'-chloromethylphenyl)-7-chlorobenzoxazole (produced by condensation of 2-amino-6-chlorophenol with 4-chloromethyl-benzoyl chloride and subsequent cyclisation in o-dichlorobenzene in the presence of p-toluenesulfonic acid, melting point 141° to 142° C.) is heated with 400 ml of triethyl phosphite in the course of 2 hours at 155° C., and the mixture is subsequently stirred at 155° to 158° C. for a further 7 hours. After cooling to 90° C., the unreacted triethyl phosphite is distilled off in vacuo. The reaction product, which is still oily, is stirred into 1000 ml of petroleum ether, and after a short time crystallisation occurs. The product is filtered off, washed with petroleum ether and dried. The yield is 210 g (97% of theory) of 2-(4'-diethylphosphonomethylphenyl)-7-chlorobenzoxazole having a melting point of 92° to 93° C.

EXAMPLE 2

If 14.1 g of 2-(4'-diethylphosphonomethylphenyl)-7-sec-butyl-benzoxazole is used instead of 13.3 g of 2-(4'-diethylphosphonomethylphenyl)-7-chlorobenzoxazole, the procedure otherwise being as given in Example 1, there is obtained the product of the formula

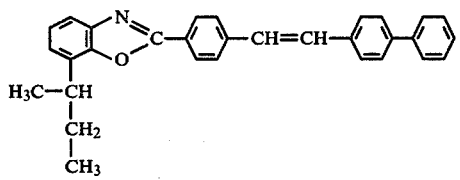
(200)

having a melting point of 187° to 188° C.

The 2-amino-6-sec-butyl required for the synthesis of the above compound is produced in the following manner:

A mixture comprising 290.6 g of 65% nitric acid and 800 g of glacial acetic acid is cooled to 0° C., and at 0° to 4° C. there is added in the course of 1½ hours, with thorough stirring and with cooling, a solution of 375.6 g of sec-butylphenol in 375 g of glacial acetic acid. There results a dark solution which is stirred at 0° to 4° C. for a further one hour. The reaction mixture is subsequently stirred into 5000 ml of water and ice. The nitrating mixture is obtained as a dark oil which is extracted with 1500 ml of chloroform. The chloroform is distilled off, and steam is passed into the dark oil obtained. As distillate is obtained 235 g of 2-nitro-6-sec-butylphenol in the form of light-yellow oil.

By the same process are obtained also 2-nitro-6-isopropylphenol (b.p. 108°–109° C.) and 2-nitro-6-alkyl-phenol (b.p.$_{10}$ 108°–109° C.).

2-Nitro-6-sec-butylphenol is converted, in a known manner, by reduction with Raney nickel into 2-amino-6-sec-butylphenol (b.p.$_{0.8}$ 151° to 154° C.).

2-Amino-6-t.-butylphenol (melting point 99° to 100° C.) is also produced by this process.

EXAMPLE 3

8.55 g of 2-(4'-methylphenyl)-7-phenyl-benzoxazole (produced by condensation of 2-amino-6-phenylphenol with 4-methyl-benzoyl chloride and subsequent cyclisation in o-dichlorobenzene in the presence of p-toluenesulfonic acid, melting point 144° to 145° C.) and 8.93 g of 4-phenylbenzaldehyde-4'-chloranil are dissolved, under nitrogen, in 150 ml of anhydrous dimethylformamide. After the addition of 6.72 g of pulverised potassium hydroxide, stirring is maintained for a further 15 minutes at room temperature. The temperature is then raised within 30 minutes to 40° to 45° C., and stirring is continued for 2 hours at this temperature. The reaction mixture is subsequently stirred into 450 ml of methanol, and the resulting precipitate is filtered off. The residue is washed with methanol, then with water and again with methanol and finally dried. The yield is 8.5 g of the compound of the formula

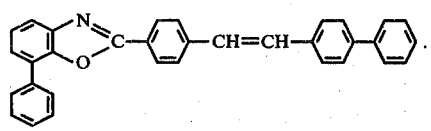
(300)

After recrystallisation from chlorobenzene in the presence of bleaching earth, the product is obtained in the form of slightly greenish-yellow crystals having a melting point of 240° to 242° C.

If instead of 2-(4'-diethylphosphonomethylphenyl)-7-chlorobenzoxazole (Example 1) there are used equimolar amounts of the phosphonates listed in Table I, column 1, with otherwise the same procedure, there are obtained the compounds shown in column 2 of Table I.

Table I

| Phosphonate | Brightener | Melting point |
|---|---|---|
| (301) | (309) | 232°–233° C. |
| (302) | (310) | 224°–225° C. |
| (303) | (311) | 226°–227° C. |
| (304) | (312) | 246°–247° C. |

Table I-continued

| Phosphonate | Brightener | Melting point |
|---|---|---|
| (305) 3-(tert-butyl)-benzoxazole-2-yl-C₆H₄-CH₂-P(O)(OC₂H₅)₂ | (313) 3-(tert-butyl)-benzoxazole-2-yl-C₆H₄-CH=CH-C₆H₄-C₆H₅ | 212°–213° C. |
| (306) 3-ethyl-benzoxazole-2-yl-C₆H₄-CH₂-P(O)(OC₂H₅)₂ | (314) 3-ethyl-benzoxazole-2-yl-C₆H₄-CH=CH-C₆H₄-C₆H₅ | 188°–189° C. |
| (307) 3-isopropyl-benzoxazole-2-yl-C₆H₄-CH₂-P(O)(OC₂H₅)₂ | (315) 3-isopropyl-benzoxazole-2-yl-C₆H₄-CH=CH-C₆H₄-C₆H₅ | 199°–200° C. |
| (308) 3-methoxy-benzoxazole-2-yl-C₆H₄-CH₂-P(O)(OC₂H₅)₂ | (316) 3-methoxy-benzoxazole-2-yl-C₆H₄-CH=CH-C₆H₄-C₆H₅ | 229°–230° C. |

The starting product for the production of the phosphonates of the formula (304) is prepared as follows:

195.52 g of 2-hydroxydiphenyl ether is dissolved in 1000 g of glacial acetic acid, and the solution is cooled to 5° C. To the formed solution is then added at 5° to 10° C. within one hour, with good cooling and thorough stirring, a solution of 104 g of a 65% nitric acid in 100 g of glacial acetic acid. The reaction mixture is stirred for a further hour at 0° to 5° C., and is subsequently stirred into a mixture of 2000 ml of water with 2000 g of ice. After the addition of 1000 g of ice, stirring in the ice-cold state is continued for some time, and the dark oil which has precipitated is separated. It is taken up in 1000 ml of chloroform, washed twice with 1000 ml of water each time, and then separated from the water. The chloroform solution is dried with anhydrous sodium sulfate, and the chloroform is distilled off in vacuo to obtain 210 g of a brown-red oil consisting mainly of 2-hydroxy-3-nitrodiphenyl ether and 2-hydroxy-5-nitrodiphenyl ether.

The products can be separated chromatographically on silica gel (solution and eluant: benzene).

The 2-hydroxy-3-nitrodiphenyl ether (melting point 65° to 66° C.) is reduced with Raney nickel to 2-hydroxy-3-aminodiphenyl ether.

EXAMPLE 4

Polyester fabric (25 g), in a ratio of goods to liquor of 1:40, is introduced into a bath containing per liter 10 g of a condensation product of aromatic sulfonic acids, 25 g of an aromatic carboxylic acid ester as the emulsifier and 5 g of sodium dihydrophosphate, and the pH value is adjusted with acetic acid to 5. After a treatment time of one hour at boiling temperature, in the presence of 0.05 g of the brightener of the formula (100) per liter, the fabric displays a brilliant brightening effect having good fastness to light.

EXAMPLE 5

100 parts of polyester granules formed from terephthalic acid ethylene glycol polyester are intimately mixed with 0.05 part of the brightener of the formula (306), and the mixture is melted at 285° C. with stirring. The spinning solution is spun out through customary spinning nozzles to obtain intensely brightened polyester fibres having good fastness to light.

The abovementioned compound can also be added to the starting materials before or during polycondensation to the polyester.

EXAMPLE 6

A polyester fabric (for example "Dacron") is padded at room temperature (about 20° C.) with an aqueous dispersion containing per liter 2 g of the brightener of the formula (200) as well as 1 g of an addition product from about 8 mols of ethylene oxide with 1 mol of p-tert-octylphenol, and drying is carried out at about 100° C. The dried material is subsequently subjected to a heat treatment at 170° to 220° C. which, depending on the temperature, has a duration varying from 2 minutes to a few seconds. The material treated in this manner exhibits an intense brightening effect having good fastness to light.

EXAMPLE 7

An intimate mixture of 100 parts of polyvinyl chloride, 3 parts of stabiliser (Advastat BD 100; Ba/Cd complex), 2 parts of titanium dioxide, 59 parts of dioctyl phthalate and 0.01 to 0.2 part of the brightener of the formula (100) is rolled out on a calendering machine at 150° to 155° C. into the form of a sheet. The opaque polyvinyl chloride sheet thus obtained has a whiteness content considerably higher than that of a sheet which does not contain the optical brightener.

EXAMPLE 8

0.06 g of ®Tinegal NA (=alkylpolyglycol ether) is added to 100 ml of water.

A solution is prepared of an optical brightener of the formula (200) by dissolving 1 g in 1000 ml of dimethylformamide. 3 ml of this stock solution is added to the above-described solution. This aqueous solution or dispersion containing the brightener is heated to 60° C. and 3 g of a nylon fabric is placed into the solution. The temperature is raised within 10 to 15 minutes to 92° to 95° C., and the bath is held at this temperature for 30 minutes. The fabric is then rinsed for 2 minutes in cold running water, and subsequently dried at 60° C. for 20 minutes. The fabric treated in this manner exhibits a distinct brightening effect which has good fastness to light.

EXAMPLE 9

Polypropylene fibres or polyethylene fibres are treated, with a ratio of goods to liquor of 1:40, with 0.02 to 0.4% of the brightener of the formula (309) for 60 minutes at 60° to 100° C. in a bath containing per liter 5 g of an addition product from about 35 mols of ethylene oxide with 1 mol of octadecyl alcohol and 0.5 g of trisodium phosphate. The material is then rinsed and dried. The polyolefine fibres obtained have a whiteness content considerably higher than that of the untreated fibres.

A similar effect is obtained by using 1 g of 85% formic acid instead of 0.5 g of trisodium phosphate.

EXAMPLE 10

100 parts of polystyrene and 0.1 part of the compound of the formula (300) are melted, with the exclusion of air, for 20 minutes at 210° C. in a tube of 1 cm diameter. The result on cooling is an optically brightened polystyrene substance having good fastness to light.

I claim:

1. A benzoxazolyl-phenyl stilbene of the formula

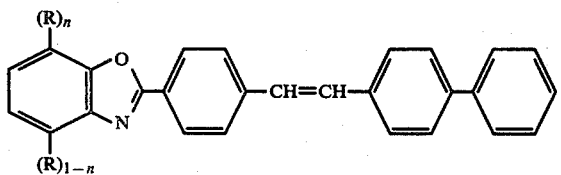

wherein
  n is the number 0 or 1, and
  R is halogen, phenyl, phenoxy or alkyl having 2 to 4 C atoms.

2. A benzoxazolyl-phenyl stilbene according to claim 1 of the formula

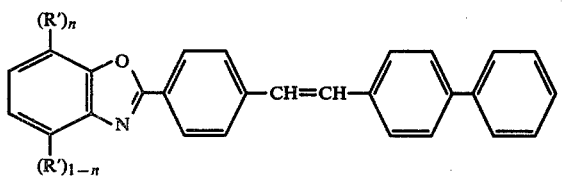

wherein
  n is the number 0 or 1, and
  R' is chlorine, phenyl, phenoxy, sec-butyl or tert-butyl.

3. A benzoxazolyl-phenyl stilbene according to claim 1 of the formula

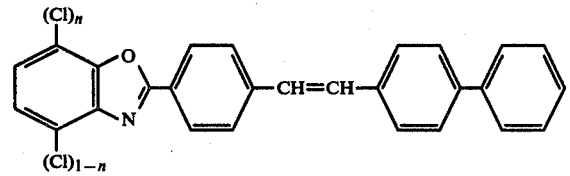

wherein n is the number 0 or 1.

4. A benzoxazolyl-phenyl stilbene according to claim 1 of the formula

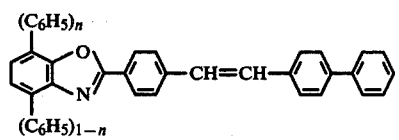

wherein n is the number 0 or 1.

5. A benzoxazolyl-phenyl stilbene according to claim 1 of the formula

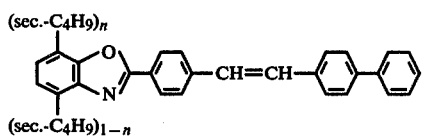

wherein n is the number 0 or 1.

6. A benzoxazolyl-phenyl stilbene according to claim 1 of the formula

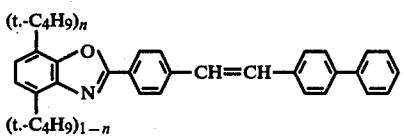

wherein n is the number 0 or 1.

7. A process for optically brightening natural and synthetic organic materials, wherein 0.005 to 2% of one of the benzoxazolyl-phenyl stilbenes defined in claim 1 is incorporated into these materials or is applied to them.

8. A process according to claim 7 for optically brightening polyester, polyester spinning solutions and polyester/cotton mixtures.

9. A process according to claim 8, wherein the organic material is optically brightened by the exhaust process.